United States Patent [19]

Gruenfeld

[11] 4,401,818
[45] Aug. 30, 1983

[54] 1-CARBOXYALKANOYL-1,2,3,4-TETRAHYDROQUINOLINE-2-CARBOXYLIC ACIDS

[75] Inventor: Norbert Gruenfeld, White Plains, N.Y.

[73] Assignee: Ciba-Geigy Corporation, Ardsley, N.Y.

[21] Appl. No.: 219,807

[22] Filed: Dec. 24, 1980

[51] Int. Cl.³ .......................................... C07D 215/16
[52] U.S. Cl. ...................................... 546/165; 424/258
[58] Field of Search ......................................... 546/165

[56] References Cited

U.S. PATENT DOCUMENTS 4,052,511  10/1977  Cashman et al. .................. 424/274

FOREIGN PATENT DOCUMENTS 29488   6/1981  European Pat. Off. .
31741   8/1981  European Pat. Off. .
3004370 8/1980  Fed. Rep. of Germany .
2937779 4/1981  Fed. Rep. of Germany .

OTHER PUBLICATIONS

J. Heterocyclic Chemistry 16, 1589, (1979).
Helv. Chim. Acta 42, 2431, (1959).

Primary Examiner—Donald G. Daus
Assistant Examiner—D. Springer
Attorney, Agent, or Firm—Norbert Gruenfeld

[57] ABSTRACT

1-Carboxy-(alkanoyl or aralkanoyl)-1,2,3,4-tetrahydroquinoline-2-carboxylic acids, e.g., those of the formula

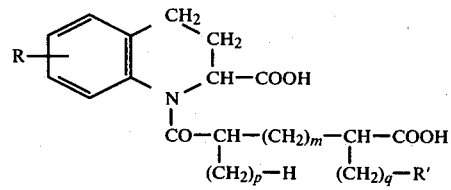

R=H, alkyl, alkoxy, halogeno or $CF_3$;
R′=H or R-phenyl;
m=0 or 1;
p,q=0 to 2;

and functional derivatives thereof, are antihypertensive and cardioactive agents.

8 Claims, No Drawings

1-CARBOXYALKANOYL-1,2,3,4-TETRAHYDROQUINOLINE-2-CARBOXYLIC ACIDS

BACKGROUND OF THE INVENTION

"Peptides containing 1,2,3,4-tetrahydroquinoline-2-carboxylic acids" are described by G. P. Zecchini et al in J. Heterocyclic Chem. 16, 1589 (1979), for the cyclization with acetic anhydride, to form "1H,3H,5H-oxazolo[3,4-a]quinolin-3-one derivatives". Also, 1-(mercapto- or acylthioalkanoyl)-1,2,3,4-tetrahydroquinoline-2-carboxylic acids, and salts thereof, are known, e.g., according to DOS No. 3,004,370, as possessing antihypertensive activity. Surprisingly it was found that by exchange of either the former mono-peptide, or the latter mercaptoalkanoyl moiety, by a carboxy-alkanoyl or aralkanoyl moiety, superior antihypertensive agents are obtained.

SUMMARY OF THE DISCLOSURE

The present invention concerns and has for its object the provision of new 1-carboxy-(alkanoyl or aralkanoyl)-1,2,3,4-tetrahydroquinoline-2-carboxylic acids, more particularly of those corresponding to Formula I:

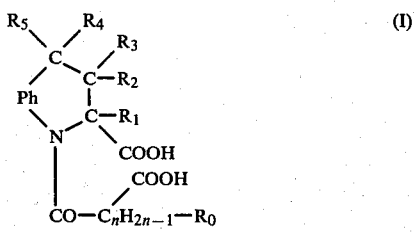

wherein Ph is unsubstituted 1,2-phenylene, or 1,2-phenylene substituted by one to three identical or different members selected from lower alkyl, lower alkoxy, lower alkylenedioxy, hydroxy, halogeno and trifluoromethyl; $R_0$ is hydrogen or HPh; each of $R_1$, $R_2$, $R_3$, $R_4$ and $R_5$ is hydrogen or lower alkyl; and n is an integer from 1 to 10; the amides mono- or di-lower alkylamides, lower alkyl esters (amino, mono- or di-lower alkylamino, carboxy or lower carbalkoxy)-lower alkyl esters, or pharmaceutically acceptable salts thereof; as well as of corresponding pharmaceutical compositions and of methods for the preparation and application of said products, which are useful antihypertensive and cardioactive agents.

DESCRIPTION OF THE PREFERRED EMBODIMENTS

The 1,2-phenylene group pH and/or the phenyl group HPh, are preferably unsubstituted or monosubstituted, and their substituents are illustrated by the following groups; lower alkyl, e.g, methyl, ethyl, n- or i-propyl or -butyl; lower alkoxy, e.g., methoxy, ethoxy, n- or i-propoxy or -butoxy; lower alkylenedioxy, e.g., methylenedioxy, 1,1- or 1,2-ethylenedioxy; hydroxy; halogeno, e.g., fluoro, chloro or bromo; or trifluoromethyl.

Each of $R_1$, $R_2$, $R_3$, $R_4$ and $R_5$ is preferably hydrogen, but also lower alkyl, advantageously methyl, or another of those mentioned previously.

The term "lower", referred to above and hereinafter in connection with organic radicals or compounds respectively, defines such with up to 7, preferably up to 4, and advantageously but one or two carbon atoms.

The alkylene or aralkylene moiety $C_n H_{2n-1}$—$R_o$ is either straight, or preferably branched, and contains advantageously up to 8 chain-carbon atoms. Thus, it represents for example, in case $R_o$=H, ethylene, 1,2- or 1,3-propylene, 2-methyl-1,2- or -1,3-propylene, 1,2-, 1,3-, 2,3- or 1,4-butylene, 1,2-, 1,3-, 1,4-, 2,4- or 1,5-pentylene; or in case $R_o$=phenyl, ω-phenyl-(1,2-, 1,3- or 2,3-propylene, -butylene or -pentylene, 1,3-, 2,3- or 2,4-butylene, -pentylene or hexylene, or 3,5-heptylene or -octylene).

Said functional derivatives, wherein either one or both carboxy groups are esterified or amidized, are preferably the mono- or bis-lower alkyl esters, e.g. the methyl, ethyl, n- or i-propyl or -butyl esters; the mono- or bis-amide, or the correspondingly N-alkylated amides, e.g. mono- or dimethylamide, or said substituted lower alkyl esters, preferably the half-esters with a free indoline-2-carboxy group, e.g. the ω-(amino, mono- or dimethylamino, carboxy or carbethoxy)-(ethyl, propyl or butyl) esters.

Pharmaceutically acceptable salts are preferably metal or ammonium salts of said acids, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium bases, e.g., methylamine, diethylamine, triethylamine, dicyclohexylamine, triethanolamine, ethylenediamine, tris-(hydroxymethyl)-aminomethane or benzyl-trimethylammonium hydroxide. Said basic (amino, mono- or di-lower alkylamino)-lower alkyl esters form also acid addition salts, which are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid.

The compounds of this invention exhibit valuable pharmacological properties, primarily hypotensive, antihypertensive and cardioactive effects, inter alia due to their angiotensin converting enzyme inhibitory activity. This is demonstrable by in vivo or in vitro animal tests, using advantageously mammals, e.g., rats, cats, dogs or isolated organs thereof, as test objects. The animals may either be normotensive or hypertensive e.g., genetically hypertensive rats, or renal hypertensive rats and dogs, and sodium-depleted dogs. Said compounds can be applied to them enterally or parenterally, advantageously orally or intravenously, for example within gelatin capsules or in the form of starchy suspensions or aqueous solutions respectively. The applied dosage may range between about 0.1 and 100 mg/kg/day, preferably between about 1 and 50 mg/kg/day.

The in vivo lowering effect on the blood pressure is recorded either directly by means of a catheter, for example placed in the dog's femoral artery, or indirectly by sphygmomanometry at the rat's tail, and a transducer, expressing the blood pressure prior and after dosing in mm Hg. Thus, for example, the representative members of the compounds of this invention, illustrated by the Examples herein, are very effective in hypertensive rats and dogs at p.o.-doses as low or lower than 50 mg/kg/day.

They also exhibit an inhibitory effect against the angiotensin I pressure response of normotensive rats. The enzyme renin, normally causes specific hydrolysis of the circulating protein renin-substrate. This hydrolysis generates angiotensin I, which is further hydrolyzed by the action of said converting enzyme to the potent vasoconstrictor angiotensin II. The inhibition of said enzyme prevents the generation of angiotensin II from I and, therefore, attenuates any pressure response following an angiotensin I challenge.

The corresponding in vivo test is performed with male, normotensive rats, which are anesthetized with 100–120 mg/kg i.p. of sodium ethyl-(1-methylpropyl)-malonylthiourea. A femoral artery and saphenous vein are cannulated for direct blood pressure measurement and i.v. administration of angiotensin I and compounds of this invention. After the basal blood pressure is stabilized, pressor responses to 3 challenges of 0.33 µg/kg of angiotensin I i.v., in 5 minute intervals, are obtained. Such pressure responses are again obtained, 5, 10, 15, 30 and 60 minutes after either i.v., or p.o. administration (stomach tube) of the compounds to be tested, and compared with the initial responses. Any observed decrease of said pressor response is an indication of angiotensin I converting enzyme inhibition, ranging up to 80% after 10 mg/kg i.v., or 50 mg/kg p.o. doses, which decrease may be sustained up to 60 minutes.

The in vitro inhibition of the angiotensin-converting enzyme by the compounds of this invention can be demonstrated analogous to Biochim. Biophys. Acta 293, 451 (1973). According to this method said compounds are dissolved at about 1 mM concentrations in phosphate buffer, externally cooled with ice. To these solutions various µl amounts of 1 mM of histidyl-leucine in phosphate buffer are added, followed by 100 µl of 5 mM hippuryl-histidyl-leucine in phosphate buffer and 50 µl of the angiotensin-converting enzyme, which is freshly prepared from lungs of adult male rabbits in Tris buffer, containing potassium and magnesium chloride, as well as sucrose. Said solutions are incubated at 37° for 30 minutes and combined with 0.75 ml of 0.6 N aqueous sodium hydroxide to stop further reaction. Then 100 µl of o-phthalaldehyde are added at room temperature, and 10 minutes later 100 µl of 6 N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the IC$_{50}$, i.e., the drug concentration which gives half the activity of the control sample containing no drug. Again, said representative members of the compounds of this invention are very effective in this in vitro test system.

Accordingly, the compounds of this invention are valuable antihypertensive agents, especially useful for ameliorating hypertension (regardless of etiology) and/or heart-conditions, such as congestive heart failure, and/or other edemic or ascitic diseases, e.g. hepatic cirrhosis. They are also useful intermediates in the preparation of other valuable products, especially of corresponding pharmaceutical compositions.

Particularly useful for said purpose are those compounds of Formula I, wherein Ph is unsubstituted 1,2-phenylene, or 1,2-phenylene substituted by one or two identical or different members selected from lower alkyl, lower alkoxy, hydroxy and halogeno, or 1,2-phenylene substituted by one lower alkylenedioxy or trifluoromethyl group; $R_o$ is hydrogen or HPh; each of $R_1$, $R_2$, $R_3$, $R_4$ and $R_5$ is hydrogen or lower alkyl; and n is an integer from 1 to 10; the amides, mono- or di-lower alkylamides, lower alkyl esters, (amino, mono- or di-lower alkylamino, carboxy or lower carbalkoxy)-lower alkyl esters, or pharmaceutically acceptable alkali metal, alkaline earth metal or ammonium salts of said acids, or acid addition salts of said aminoalkyl esters.

More preferred are those of compounds of Formula I, wherein Ph is 1,2-phenylene, unsubstituted or monosubstituted by lower alkyl, lower alkoxy, lower alkylenedioxy, hydroxy, halogeno or trifluoromethyl; $R_o$ is hydrogen or HPh; each of $R_1$, $R_2$, $R_3$, $R_4$ and $R_5$ is hydrogen or methyl; and n is an integer from 2 to 8; and said functional acid and amino derivatives listed in the previous paragraph.

Especially valuable compounds of this invention are those of Formula II

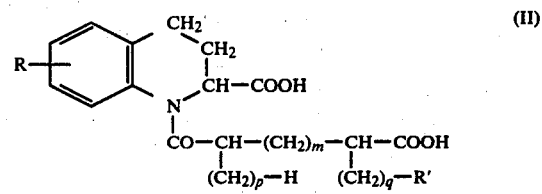

more specifically the tetrahydroquinoline-2S-chiral epimers thereof, wherein R is hydrogen, alkyl or alkoxy with up to 4 carbon atoms, halogeno or trifluoromethyl; m is the integer 0 or 1; each of p and q is an integer from 0 to 2; and R' is hydrogen or R-phenyl; the mono- or bis-amide, the mono- or bis-lower (alkyl or ω-aminoalkyl) esters, pharmaceutically acceptable alkali metal or ammonium salts of said acids or acid addition salts of said aminoalkyl esters.

The most preferred compounds of this invention are those of Formula II, wherein R is hydrogen, methyl, methoxy, fluoro, chloro or trifluoromethyl, advantageously in the 6-position, each of m and p is the integer 1, q is the integer 1 or 2, and R' is hydrogen or phenyl, or said functional acid derivatives listed in the preceding paragraph.

The compounds of this invention are prepared according to conventional methods, advantageously by:

(1) condensing a compound of Formula III

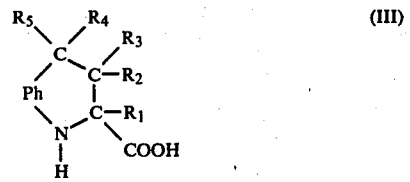

or said acid or amino derivatives thereof, with a reactive functional derivative of a compound of Formula IV

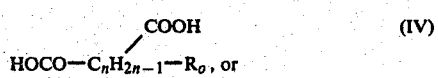

(IV)

(2) hydrolysing or alcoholyzing a compound of Formula V

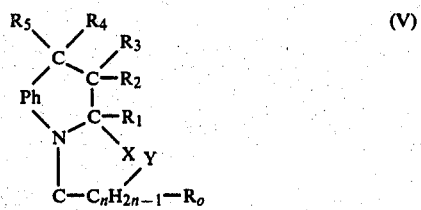

(V)

wherein at least one of X and Y is cyano, and the other is said free, amidized or esterified carboxy group; and if desired, converting any resulting compound into another compound of this invention.

Reactive functional derivatives of compounds IV are preferably ester-halides, simple or mixed anhydrides, such as the lower alkyl half esters of said acid chlorides, the cyclic anhydride, or mixed acetic or cyanoacetic anhydrides. Said condensation of compounds III and IV occurs either spontaneously, or in the presence of condensing agents, such as organic or inorganic bases, e.g. said salt-forming amines or alkali metal carbonates, or disubstituted carbodiimides. Both starting materials III and IV are known, or if new, may be prepared according to the illustrative examples herein.

Said hydrolysis of the nitriles V to the corresponding acids or amides is advantageously carried out with inorganic acids, such as hydrohalic or sulfuric acids, in known manner; and said alcoholysis is analogously performed in the presence of both said acids and the corresponding unsubstituted or substituted lower alkanols. Said starting material V may be obtained analogous to process 1, from the known compounds III, and the corresponding nitriles of IV.

The compounds of the invention so obtained, can be converted into each other according to conventional methods. Thus, for example, resulting amides or esters may be further hydrolyzed or alcoholyzed (transesterified) according to process 2), or with aqueous alkalies, such as alkali metal carbonates or hydroxides, respectively. Resulting free acids may be esterified with said unsubstituted or substituted lower alkanols or diazoalkanes, or converted into said metal, ammonium or acid addition salts in conventional manner.

Thus, for example, any resulting free acid or base can be converted into a corresponding metal, ammonium or acid addition salt respectively, by reacting it with an equivalent amount of the corresponding base, basic salt, acid or ion exchange preparation, e.g. said acids with alkali or ammonium hydroxides or carbonates, or said aminoalkyl esters with said inorganic or organic acids respectively. Any resulting salt may also be converted into the free compounds, by liberating the latter with stronger acids or bases respectively. In view of the close relationship between the free compounds, and the salts thereof, whenever a compound of the invention, or intermediate thereof, is referred to in this context, a corresponding salt is also intended, provided such is possible or appropriate under the circumstances.

In case mixtures of geometrical or optical isomers of the above compounds of Formulae I to V are obtained, these can be separated into the single isomers by methods in themselves known, e.g., by fractional distillation, crystallization and/or chromatography. Racemic products can likewise be resolved into the optical antipodes, for example, by separation of diastereomeric salts thereof, such as according to J. Org. Chem. 43, 3803 (1978), e.g., by the fractional crystallization of d-or l-(tartrates, mandelates, camphorsulfonates, or 1-naphthyl-1-ethylisocyanates), or of d- or l-(α-methylbenzylammonium, cinchonidine, cinchonine, quinine, quinidine, ephedrine, dehydroabiethylamine, brucine or strychnine)-salts. The preferred starting material of Formula III is the 2-S-optical isomer (epimer) thereof.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably at the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g., those of Formula II, and being the following chiral isomers.

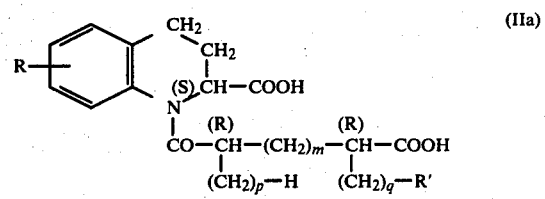

(IIa)

The pharmacologically active compounds of the invention are useful in the manufacture of pharmaceutical compositions comprising an effective amount thereof in conjunction or admixture with excipients suitable for either enteral or parenteral administration. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, or effervescent mixtures and/or (e) absorbents, colorants, flavors and sweeteners. Injectable compositions are preferably aqueous isotonic solutions or suspensions; and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances, e.g. other antihypertensive agents and/or diuretics. Said compositions are prepared according to conventional mixing, granulating or coating methods respectively, and contain about 0.1 to 75%, preferably about 1 to 50% of the active ingredient. A unit dosage for a mammal of about 50-70 kg weight may contain between about 5 and 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

The mixture of 1.0 g of 1,2,3,4-tetrahydroquinoline-2-carboxylic acid methyl ester (Ber. 61,2377), 0.87 g of 4-carbomethoxy-2-methylbutanoyl chloride, 1.44 g of powdered potassium carbonate and 20 ml of methylene chloride is stirred at room temperature overnight. It is cooled with ice, and 50 ml of water are added. The organic layer is separated, washed with N-hydrochloric acid and water, dried and evaporated, to yield the 1-(4-carbomethoxy-2-methylbutanoyl)-1,2,3,4-tetrahydroquinoline-2-carboxylic acid methyl ester, showing NMR-peaks at 0.85, 1.25, 3.35, 3.65 and 3.75 ppm.

The starting material is prepared as follows: 9.64 g of oxalyl chloride are added to the solution of 6.1 g of 4-carbomethoxy-2-methylbutanoic acid (U.S. Pat. No. 4,052,511) in 50 ml of methylene chloride. The mixture is refluxed for two hours and evaporated, to yield the 4-carbomethoxy-2-methylbutanoyl chloride, which is used as such without further purification.

EXAMPLE 2

To the solution of 1.5 g of 1-(4-carbomethoxy-2-methylbutanoyl)-1,2,3,4-tetrahydroquinoline-2-carboxylic acid methyl ester in 13.5 ml of methanol is added 13.5 ml of N aqueous sodium hydroxide and the mixture is stirred at room temperature for 3 hours. It is concentrated at room temperature and reduced pressure, the aqueous solution filtered, cooled and acidified with concentrated hydrochloric acid. The mixture is extracted with methylene chloride, the extract dried, evaporated, the residue recrystallized from petroleum ether and triturated with diethyl ether, to yield the 1-(4-carboxy-2-methylbutanoyl)-1,2,3,4-tetrahydroquinoline-2-carboxylic acid melting at 117°-119°.

EXAMPLE 3

The solution of 1.0 g of 1,2,3,4-tetrahydroquinoline-2-carboxylic acid methyl ester and 0.98 g of 2-(2-phenethyl)-glutaric anhydride in 10 ml of toluene, is heated to 70° for 2 days under nitrogen. It is washed with N hydrochloric acid, then with water, and extracted with 5% aqueous sodium bicarbonate. The extract is filtered, acidified with 6 N hydrochloric acid and reextracted with methylene chloride. The organic extract is dried, evaporated, the residue dissolved in 15 ml of diethyl ether and the solution combined with that of 2 ml of dicyclohexylamine in 15 ml of hexane. The resulting precipitate is filtered off and dried, to yield the dicyclohexylammonium 1-[4-carboxy-4-(2-phenethyl)-butanoyl]-1,2,3,4-tetrahydroquinoline-2-carboxylic acid methyl ester, melting at 110°-112°. It may be re-converted to the free acid with N hydrochloric acid.

The starting material is prepared as follows: The solution of 12 g of 2-(2-phenyethyl)-glutaric acid [J. Chem. Soc. 1950, 1683] in 75 ml of acetic acid anhydride is refluxed for 4 hours and evaporated. The residue is crystallized from diethyl ether, to yield the corresponding anhydride melting at 78°-80°.

EXAMPLE 4

The suspension of 1.0 g of dicyclohexylammonium 1-[4-carboxy-4-(2-phenethyl)-butanoyl]-1,2,3,4-tetrahydroquinoline-2-carboxylic acid methyl ester in 50 ml of N hydrochloric-acid-ethyl acetate (1:1) is stirred at room temperature overnight. The organic layer is separated, the aqueous solution extracted with ethyl acetate and the combined extracts evaporated. The residue is dissolved in 4.8 ml of methanol and 4.8 ml of N aqueous sodium hydroxide, and the solution stirred at room temperature for 3 hours. It is concentrated, the aqueous concentrate filtered, acidified with 6 N hydrochloric acid and extracted with methylene chloride. The extract is dried, evaporated and the residue crystallized from petroleum ether, to yield the 1-[4-carboxy-4-(2-phenethyl)-butanoyl]-1,2,3,4-tetrahydroquinoline-2-carboxylic acid melting at 58°-60°.

EXAMPLE 5

According to the methods illustrated by the previous examples, the following 1-(carboxyalkanoyl or -aralkanoyl)-1,2,3,4-tetrahydroquinoline-2-carboxylic acids are prepared:

a. 1-(4-carboxybutanoyl)-1,2,3,4-tetrahydroquinoline-2-carboxylic acid methyl ester, m.p. 122°-4°;
b. 1-(4-carboxy-2R-methylbutanoyl)-1,2,3,4-tetrahydroquinoline-2S-carboxylic acid, NMR-peaks at 1.2 and 5.1 ppm;
c. 1-(4-carboxy-2R,4R-dimethylbutanoyl)-1,2,3,4-tetrahydroquinoline-2S-carboxylic acid, NMR-peaks at 1.0, 1.2 and 5.1 ppm;
d. 1-(4-carbethoxy-2R-methylbutanoyl)-1,2,3,4-tetrahydroquinoline-2S-carboxylic acid methyl ester, NMR-peaks at 1.2, 3.6 and 5.1 ppm;
e. 1-(4-carbethoxy-2R,4R-dimethylbutanoyl)-1,2,3,4-tetrahydroquinoline-2-carboxylic acid methyl ester, NMR-peaks at 1.0, 1.2 and 3.6;
f. 1-[4-carboxy-2-methyl-4-(2-phenethyl)-butanoyl]-1,2,3,4-tetrahydroquinoline-2S-carboxylic, NMR-peaks at 1.2, 5.2 and 7.2 ppm.

The starting material can be prepared as follows:

(b) 4-Carbethoxy-2R-methylbutanoyl chloride is prepared as shown above, starting with 2R-methylglutaric acid [J. Am. Chem. Soc., 77, 3383 (1955); Arkiv for Kemi 24A (32), 1-10 (1974)].

(c) (−)2R,4R-dimethylglutaric acid (Beilstein, Handbook of Organic Chemistry, Vol. 2, Suppl. 3, p. 1755) is converted with acetyl chloride to the 2R,4R-dimethylglutaric anhydride, m.p. 43°-45°; $[\alpha]_D^{25} = +56.5°$ (c=1 in chloroform), followed by treatment with ethanol to yield the 4-carbethoxy-2R,4R-dimethylbutanoic acid as an oil; $[\alpha]_D^{25} = -49.5°$ (c=1 in ethanol). Reaction with oxalyl chloride as shown above, yields said corresponding acid chloride.

(d) N-Benzyloxycarbonyl-(S)-alanyl-1,2,3,4-tetrahydroquinoline-2S-carboxylic acid [J. Het. Chem. 16, 1589 (1979)] is first treated with 6 N hydrochloric acid/acetic acid, and subsequently with methanol/sulfuric acid, to give the 1,2,3,4-tetrahydroquinoline-2S-carboxylic acid methyl ester (J. Chem. Soc. Perkin I, 1977, 596).

EXAMPLE 6

Preparation of 10,000 tablets each containing 5 mg of the active ingredient of Example 4:

Formula

| | |
|---|---|
| 1-[4-carboxy-4-(2-phenethyl)-butanoyl]-1,2,3,4-tetrahydroquinoline-2-carboxylic acid | 50.00 g |
| Lactose | 1,157.00 g |
| Corn starch | 75.00 g |
| Polyethylene glycol 6,000 | 75.00 g |
| Talcum powder | 5.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 7

Preparation of 10,000 capsules each containing 10 mg of the active ingredient of Example 2:

Formula

| | |
|---|---|
| 1-(4-carboxy-2-methylbutanoyl)-1,2,3,4-tetrahydroquinoline-2-carboxylic acid | 100.00 g |
| Lactose | 1,800.00 g |
| Talcum powder | 100.00 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine. Analogously tablets or capsules are prepared from the remaining compounds of the invention, e.g., those illustrated by the other examples herein.

I claim:

1. A 1-carboxy-(alkanoyl or aralkanoyl)-1,2,3,4-tetrahydroquinoline-2-carboxylic acid compound of the formula:

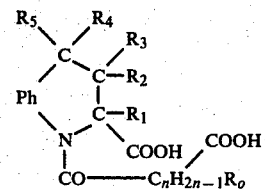

wherein Ph is unsubstituted 1,2-phenylene, or 1,2-phenylene substituted by one or two members selected from lower alkyl of 1 to 3 carbon atoms, lower alkoxy of 1 to 3 carbon atoms, hydroxy and halogeno, or 1,2-phenylene substituted by one lower alkylenedioxy of 1 to 2 carbon atoms or one trifluoromethyl group; $R_o$ is hydrogen or HPh; each of $R_1$, $R_2$, $R_3$, $R_4$ and $R_5$ is hydrogen or lower alkyl of 1 to 3 carbon atoms; $C_nH_{2n}$ represents straight chain or branched alkylene of 2 to 8 carbon atoms; the lower alkyl esters of 1 to 4 carbon atoms or pharmaceutically acceptable alkali metal, alkaline earth metal or ammonium salts of said acids.

2. A compound as claimed in claim 1, wherein Ph is 1,2-phenylene unsubstituted or mono-substituted by methyl, methoxy, methylenedioxy, hydroxy, chloro or trifluoromethyl; and each of $R_1$, $R_2$, $R_3$, $R_4$ and $R_5$ is hydrogen or methyl.

3. A compound as claimed in claim 1 and corresponding to the formula

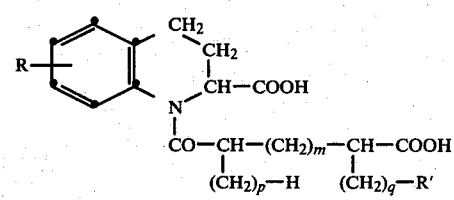

wherein R is hydrogen, alkyl or alkoxy with up to 3 carbon atoms, halogeno or trifluoromethyl; m is the integer 0 or 1; each of p and q is an integer from 0 to 2; and R' is hydrogen or R-phenyl; the mono- or bis-lower alkyl esters with up to 4 carbon atoms, pharmaceutically acceptable alkali metal or ammonium salts of said acids.

4. A compound as claimed in claim 3, in which formula R is hydrogen, methyl, methoxy, fluoro, chloro or trifluoromethyl; each of m and p is the integer 1; q is the integer 1 or 2; and R' is hydrogen or phenyl, and said acid derivatives listed in claim 3.

5. A compound as claimed in claim 3, wherein R is in the 6-tetrahydroquinoline-position.

6. A compound as claimed in claim 3, in the form of its 2S-carboxy-tetrahydroquinoline chiral epimer.

7. A compound as claimed in claim 3, and being the 1-(4-carboxy-2-methylbutanoyl)-1,2,3,4-tetrahydroquinoline-2-carboxylic acid; or a pharmaceutically acceptable alkali metal, ammonium or acid addition salt thereof.

8. A compound as claimed in claim 3, and being the 1-[4-carboxy-4-(2-phenethyl)-butanoyl]-1,2,3,4-tetrahydroquinoline-2-carboxylic acid; or a pharmaceutically acceptable alkali metal, ammonium or acid addition salt thereof.

* * * * *